US00PP11349P

United States Patent [19]

Babikow

[11] Patent Number: Plant 11,349

[45] Date of Patent: Apr. 11, 2000

[54] PORTULACA PLANT NAMED 'EULALIE'

[76] Inventor: Oliver W. Babikow, 1509 Mission Rd., Lancaster, Pa. 17691

[21] Appl. No.: 09/145,850

[22] Filed: Sep. 3, 1998

[51] Int. Cl.[7] ..... A01H 5/00

[52] U.S. Cl. ..... Plt./263

[58] Field of Search ..... Plt./263

*Primary Examiner*—Elizabeth F. McElwain
*Assistant Examiner*—Wendy A Baker
*Attorney, Agent, or Firm*—C. A. Whealy

[57] ABSTRACT

A distinct cultivar of Portulaca plant named 'Eulalie', characterized by its unique pink and white bi-colored flowers; decumbent and freely branching growth habit; and exceptional weather tolerance, plants very tolerant to rain and high temperatures.

2 Drawing Sheets

BACKGROUND OF THE INVENTION

The present invention relates to a new and distinct cultivar of Portulaca plant, botanically known as *Portulaca grandiflora,* and hereinafter referred to by the cultivar name Eulalie. The new Portulaca is marketed under the name Giant Bi-Color.

The new Portulaca is a naturally-occurring whole plant mutation of *Portulaca grandiflora* cultivar Samba (not patented). The new Portulaca was discovered and selected by the Inventor as a flowering plant within a population of plants of the cultivar Samba grown in a cultivated area in Leola, Pa. The new Portulaca was selected on the basis of its unique pink and white bi-colored flowers.

Asexual reproduction of the new cultivar by terminal cuttings taken at Homer City, Pa., has shown that the unique features of this new Portulaca are stable and reproduced true to type in successive generations.

SUMMARY OF THE INVENTION

Plants of the cultivar Eulalie have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Eulalie'. These characteristics in combination distinguish 'Eulalie' as a new and distinct cultivar:

1. Unique pink and white bi-colored flowers.
2. Decumbent and freely branching growth habit.
3. Exceptional weather tolerance; very tolerant to rain and high temperatures.

Plants of the cultivar Eulalie are similar in plant form to plants of the parent cultivar Samba, however vary in flower color as flower color of plants of 'Samba' are solid pink (R.H.S. 74B) in color and are not bi-colored.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a top perspective view of a typical hanging basket plant of the new Portulaca.

The photograph on the second sheet comprises a close-up view of a typical flower and leaves of the new Portulaca.

Flower and foliage colors in the photographs may appear different than the actual colors due to light reflectance and shadows

DETAILED BOTANICAL DESCRIPTION

In the following description, color references are made to The Royal Horticultural Society Colour Chart except where general terms of ordinary dictionary significance are used. Plants used for the description were grown for about 16 to 18 weeks in greenhouses under typical production conditions in 25-cm hanging baskets during the late spring in Homer City, Pa., and during the summer in Roanoke, Tex.

Botanical classification: *Portulaca grandiflora* cultivar Eulalie.

Parentage: Naturally-occurring whole plant mutation of *Portulaca grandiflora* cultivar Samba (not patented).

Propagation:

- *Type cutting.*—Terminal vegetative cuttings.
- *Time to initiate and develop roots, summer.*—About 14 to 16 days at 18° C.
- *Time to initiate and develop roots, winter.*—About 20 days at 10° C.
- *Rooting habit.*—Numerous, fine, fibrous, and well-branched.

Plant description:

- *Form.*—Decumbent, very suitable for hanging basket containers.
- *Branching habit.*—Freely branching, lateral branches may form at every node.
- *Plant height (from soil level to top of plant plane).*—About 13.5 cm.
- *Plant diameter.*—About 60 cm, indeterminate.
- *Vigor.*—Vigorous.
- *Foliage description.*—Leaves simple, generally symmetrical and long persisting. Leaves usually alternate, whorled below flowers at terminal apices; fleshy, succulent. Length: About 2.2 cm. Width: About 2 mm. Thickness: About 1.2 mm. Aspect: Perpendicular to stem. Shape: Acicular, cylindrical. Apex: Sharply acute. Base: Attenuate. Margin: Entire. Texture: Pubescence at leaf nodes. Color: Young foliage upper surface: 146A. Young foliage lower surface: 146A to 146B. Mature foliage upper surface: 147A. Mature foliage lower surface: 147A to 147B. Petiole: Length: About 3 mm. Diameter: About 1.5 mm. Texture: Pubescent. Color: 146D to light greenish white.

*Stem description.*—Diameter: About 2 mm. Internode length: About 1 cm. Shape: Cylindrical. Color: 146A to 146C with red overtones.

Flower description:

*Flower type and habit.*—Large cupped pink and white bi-colored single flowers that face upwards, terminal subtended by an involucre of leaves.

*Natural flowering season.*—Continuously flowers from spring through fall.

*Flower longevity.*—Typically about one week.

*Quantity.*—Numerous flowers per plant.

*Flower size.*—Diameter: About 6.5 cm. Height: About 1.5 cm.

*Petals.*—Quantity: Typically four. Length: About 3.1 cm. Width: About 2.8 cm. Shape: Typically cordate. Margin: Entire, emarginate at apex. Texture: Very smooth, satiny, iridescent. Color: Pink and white bi-colored, colors bleed together in streaks. Petal color, upper surface: Base, dark pink, 72A to 72B; center, pink, 72B to 72D and 77B to 77C; white towards margin, 155D. Petal color, lower surface: Base, dark pink, 72A to 72B; center, pink, 72C to 72D and 77B to 77C; white towards margin, 155D.

*Sepals.*—Quantity: Two. Length: About 1.3 cm. Width: About 7 mm. Shape: Deltoid. Apex: Acute. Margin: Entire. Aspect: Upright. Texture: Smooth. Color: 144B to 144C.

*Reproductive organs.*—Stamens: Stamen number: Numerous. Anther length: About 1 mm. Filament length: About 1 cm. Filament color: White at base; pink, 72B to 72C, towards apex. Pollen amount: Abundant. Pollen color: 21A. Pistils: Pistil length: About 1.4 cm. Stigma shape: Typically seven-parted. Stigma color: White. Style color: Greenish white at base; pink, 72B to 72C, towards apex.

Disease resistance: No resistance to diseases common to Portulaca has been observed.

Seed production: Seed production has not been observed.

It is claimed:

1. A new and distinct cultivar of Portulaca plant named 'Eulalie', as illustrated and described.

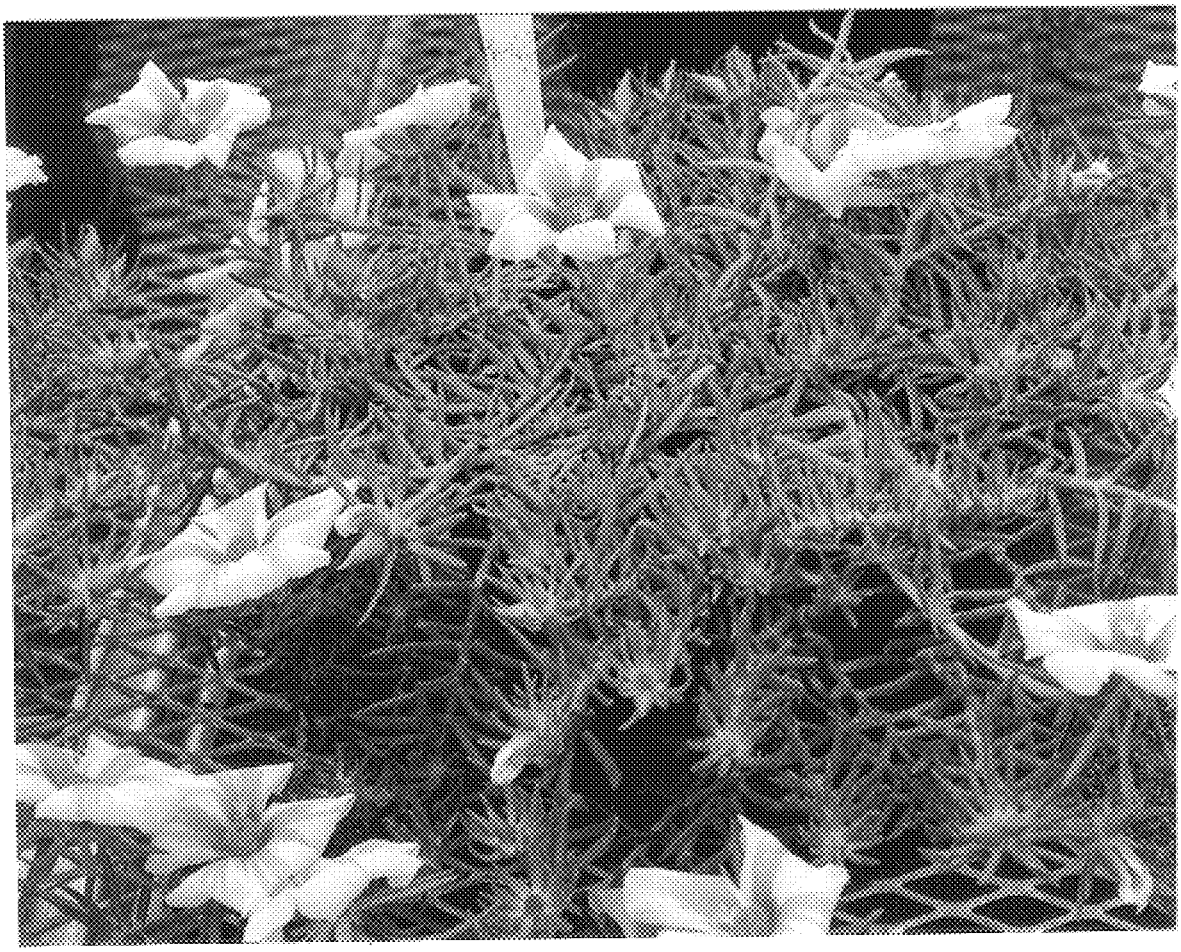

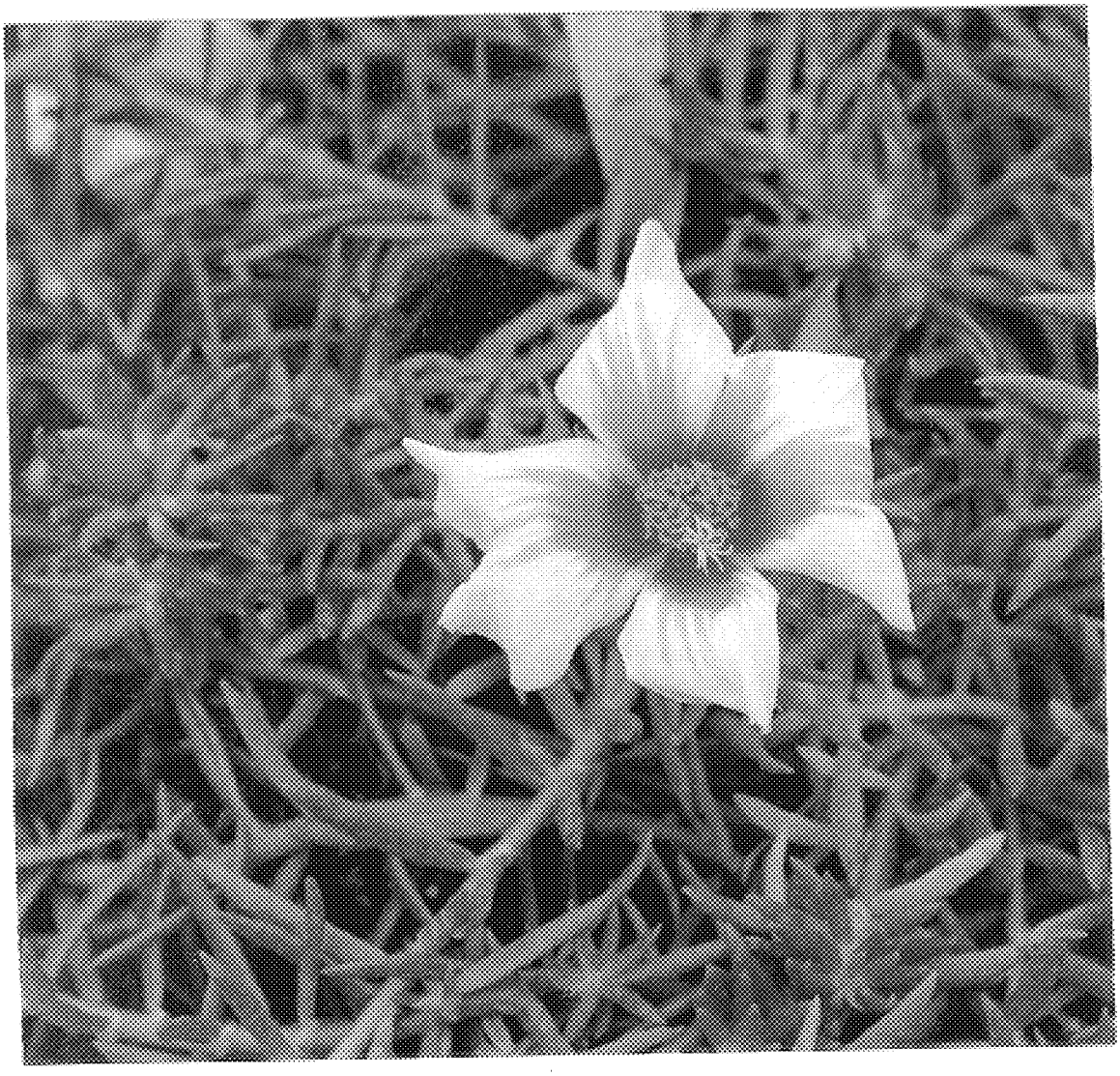

* * * * *